(12) United States Patent
Casanova et al.

(10) Patent No.: US 9,579,077 B2
(45) Date of Patent: Feb. 28, 2017

(54) MULTIPLE IMAGING MODE TISSUE MARKER

(75) Inventors: R. Michael Casanova, Scottsdale, AZ (US); Dnyanesh A. Talpade, Kinnelon, NJ (US); Chandrashekhar P. Pathak, Phoenix, AZ (US)

(73) Assignee: C.R. Bard, Inc., Murray Hill, NJ (US)

( * ) Notice: Subject to any disclaimer, the term of this patent is extended or adjusted under 35 U.S.C. 154(b) by 1086 days.

(21) Appl. No.: 12/518,695

(22) PCT Filed: Dec. 12, 2007

(86) PCT No.: PCT/US2007/087211
§ 371 (c)(1),
(2), (4) Date: Jun. 11, 2009

(87) PCT Pub. No.: WO2008/073965
PCT Pub. Date: Jun. 19, 2008

(65) Prior Publication Data
US 2010/0030072 A1 Feb. 4, 2010

Related U.S. Application Data

(60) Provisional application No. 60/869,636, filed on Dec. 12, 2006.

(51) Int. Cl.
*A61B 5/05* (2006.01)
*A61B 6/00* (2006.01)
*A61B 8/08* (2006.01)

(52) U.S. Cl.
CPC .............. *A61B 6/481* (2013.01); *A61B 8/481* (2013.01); *A61B 90/39* (2016.02); *A61B 2090/376* (2016.02); *A61B 2090/3908* (2016.02); *A61B 2090/3925* (2016.02); *A61B 2090/3995* (2016.02)

(58) Field of Classification Search
CPC ............. A61B 8/481; A61B 8/00; A61B 6/12; A61B 10/02; A61B 2017/00004; A61B 19/00
USPC ... 600/414, 420, 424, 426, 431; 424/9.4, 9.5
See application file for complete search history.

(56) References Cited

U.S. PATENT DOCUMENTS

| 2,192,270 A | 3/1940 | McGowan |
| 2,481,408 A | 9/1949 | Fuller et al. |
| 2,832,888 A | 4/1958 | Houston |

(Continued)

FOREIGN PATENT DOCUMENTS

| DE | 1029528 B | 5/1958 |
| EP | 0146699 A1 | 7/1985 |

(Continued)

OTHER PUBLICATIONS

Press release for Biopsys Ethicon Endo-Surgery (Europe) GmbH; The Mammotome Vacuum Biopsy System. From: http://www.medicine-news.com/articles/devices/mammotome.html. 3 pages.

(Continued)

*Primary Examiner* — Joel Lamprecht

(57) ABSTRACT

An intracorporeal marker for marking a site within living tissue of a host having a body of porous hydroxyapatite whose physical properties permit the body to be distinguished from human soft tissue under visualization using ultrasonic and radiation imaging modalities.

11 Claims, 1 Drawing Sheet

(56) References Cited

U.S. PATENT DOCUMENTS

| | | |
|---|---|---|
| 2,899,362 A | 8/1959 | Sieger, Jr. et al. |
| 2,907,327 A | 10/1959 | White |
| 3,341,417 A | 9/1967 | Sinaiko |
| 3,402,712 A | 9/1968 | Eisenhand |
| 3,516,412 A | 6/1970 | Ackerman |
| 3,593,343 A | 7/1971 | Viggers |
| 3,757,781 A | 9/1973 | Smart |
| 3,818,894 A | 6/1974 | Wichterle et al. |
| 3,823,212 A | 7/1974 | Chvapil |
| 3,921,632 A | 11/1975 | Bardani |
| 4,005,699 A | 2/1977 | Bucalo |
| 4,007,732 A | 2/1977 | Kvavle et al. |
| 4,041,931 A | 8/1977 | Elliott et al. |
| 4,103,690 A | 8/1978 | Harris |
| 4,105,030 A | 8/1978 | Kercso |
| 4,172,449 A | 10/1979 | LeRoy et al. |
| 4,197,846 A | 4/1980 | Bucalo |
| 4,217,889 A | 8/1980 | Radovan et al. |
| 4,276,885 A | 7/1981 | Tickner et al. |
| 4,294,241 A | 10/1981 | Miyata |
| 4,298,998 A | 11/1981 | Naficy |
| 4,331,654 A | 5/1982 | Morris |
| 4,390,018 A | 6/1983 | Zukowski |
| 4,400,170 A | 8/1983 | McNaughton et al. |
| 4,401,124 A | 8/1983 | Guess et al. |
| 4,405,314 A | 9/1983 | Cope |
| 4,428,082 A | 1/1984 | Naficy |
| 4,438,253 A | 3/1984 | Casey et al. |
| 4,442,843 A | 4/1984 | Rasor et al. |
| 4,470,160 A | 9/1984 | Cavon |
| 4,487,209 A | 12/1984 | Mehl |
| 4,545,367 A | 10/1985 | Tucci |
| 4,549,560 A | 10/1985 | Andis |
| 4,582,061 A | 4/1986 | Fry |
| 4,582,640 A | 4/1986 | Smestad et al. |
| 4,588,395 A | 5/1986 | Lemelson |
| 4,597,753 A | 7/1986 | Turley |
| 4,647,480 A | 3/1987 | Ahmed |
| 4,655,226 A | 4/1987 | Lee |
| 4,661,103 A | 4/1987 | Harman |
| 4,682,606 A | 7/1987 | DeCaprio |
| 4,693,237 A | 9/1987 | Hoffman et al. |
| 4,740,208 A | 4/1988 | Cavon |
| 4,762,128 A | 8/1988 | Rosenbluth |
| 4,813,062 A | 3/1989 | Gilpatrick |
| 4,820,267 A | 4/1989 | Harman |
| 4,832,680 A | 5/1989 | Haber et al. |
| 4,832,686 A | 5/1989 | Anderson |
| 4,847,049 A | 7/1989 | Yamamoto |
| 4,863,470 A | 9/1989 | Carter |
| 4,870,966 A | 10/1989 | Dellon et al. |
| 4,874,376 A | 10/1989 | Hawkins, Jr. |
| 4,889,707 A | 12/1989 | Day et al. |
| 4,909,250 A | 3/1990 | Smith |
| 4,938,763 A | 7/1990 | Dunn et al. |
| 4,950,665 A | 8/1990 | Floyd |
| 4,963,150 A | 10/1990 | Brauman |
| 4,970,298 A | 11/1990 | Silver et al. |
| 4,989,608 A | 2/1991 | Ratner |
| 4,994,013 A | 2/1991 | Suthanthiran et al. |
| 4,994,028 A | 2/1991 | Leonard et al. |
| 5,012,818 A | 5/1991 | Joishy |
| 5,059,197 A | 10/1991 | Urie et al. |
| 5,081,997 A | 1/1992 | Bosley, Jr. et al. |
| 5,120,802 A | 6/1992 | Mares et al. |
| 5,125,413 A | 6/1992 | Baran |
| 5,137,928 A | 8/1992 | Erbel et al. |
| 5,141,748 A | 8/1992 | Rizzo |
| 5,147,307 A | 9/1992 | Gluck |
| 5,147,631 A | 9/1992 | Glajch et al. |
| 5,162,430 A | 11/1992 | Rhee et al. |
| 5,163,896 A | 11/1992 | Suthanthiran et al. |
| 5,195,540 A | 3/1993 | Shiber |
| 5,197,482 A | 3/1993 | Rank et al. |
| 5,197,846 A | 3/1993 | Uno et al. |
| 5,199,441 A | 4/1993 | Hogle |
| 5,219,339 A | 6/1993 | Saito |
| 5,221,269 A | 6/1993 | Miller et al. |
| 5,231,615 A | 7/1993 | Endoh |
| 5,236,410 A | 8/1993 | Granov et al. |
| 5,242,759 A | 9/1993 | Hall |
| 5,250,026 A | 10/1993 | Ehrlich et al. |
| 5,271,961 A | 12/1993 | Mathiowitz et al. |
| 5,273,532 A | 12/1993 | Niezink et al. |
| 5,280,788 A | 1/1994 | Janes et al. |
| 5,281,197 A | 1/1994 | Arias et al. |
| 5,281,408 A | 1/1994 | Unger |
| 5,282,781 A | 2/1994 | Liprie |
| 5,284,479 A | 2/1994 | de Jong |
| 5,289,831 A | 3/1994 | Bosley |
| 5,320,100 A | 6/1994 | Herweck et al. |
| 5,320,613 A | 6/1994 | Houge et al. |
| 5,328,955 A | 7/1994 | Rhee et al. |
| 5,334,381 A | 8/1994 | Unger |
| 5,344,640 A | 9/1994 | Deutsch et al. |
| 5,353,804 A | 10/1994 | Kornberg et al. |
| 5,354,623 A | 10/1994 | Hall |
| 5,358,514 A | 10/1994 | Schulman et al. |
| 5,366,756 A | 11/1994 | Chesterfield et al. |
| 5,368,030 A | 11/1994 | Zinreich et al. |
| 5,388,588 A | 2/1995 | Nabai et al. |
| 5,394,875 A | 3/1995 | Lewis et al. |
| 5,395,319 A | 3/1995 | Hirsch et al. |
| 5,409,004 A | 4/1995 | Sloan |
| 5,417,708 A | 5/1995 | Hall et al. |
| 5,422,730 A | 6/1995 | Barlow et al. |
| 5,425,366 A | 6/1995 | Reinhardt et al. |
| 5,431,639 A | 7/1995 | Shaw |
| 5,433,204 A | 7/1995 | Olson |
| 5,449,560 A | 9/1995 | Antheunis et al. |
| 5,451,406 A | 9/1995 | Lawin et al. |
| 5,460,182 A | 10/1995 | Goodman et al. |
| 5,469,847 A * | 11/1995 | Zinreich et al. ............... 600/414 |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |
| 5,542,915 A | 8/1996 | Edwards et al. |
| 5,549,560 A | 8/1996 | Van de Wijdeven |
| RE35,391 E | 12/1996 | Brauman |
| 5,580,568 A | 12/1996 | Greff et al. |
| 5,585,112 A | 12/1996 | Unger et al. |
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |
| 5,636,255 A | 6/1997 | Ellis |
| 5,643,246 A | 7/1997 | Leeb et al. |
| 5,646,146 A | 7/1997 | Faarup et al. |
| 5,665,092 A | 9/1997 | Mangiardi et al. |
| 5,667,767 A | 9/1997 | Greff et al. |
| 5,669,882 A | 9/1997 | Pyles |
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,716 A | 12/1997 | Dunn et al. |
| 5,716,981 A | 2/1998 | Hunter et al. |
| 5,747,060 A | 5/1998 | Sackler et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,775 A | 7/1998 | Milliman et al. |
| 5,795,308 A | 8/1998 | Russin |

(56) References Cited

U.S. PATENT DOCUMENTS

| | | |
|---|---|---|
| 5,799,099 A | 8/1998 | Wang et al. |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,826,776 A | 10/1998 | Schulze et al. |
| 5,830,178 A | 11/1998 | Jones et al. |
| 5,842,477 A | 12/1998 | Naughton et al. |
| 5,842,999 A | 12/1998 | Pruitt et al. |
| 5,845,646 A | 12/1998 | Lemelson |
| 5,846,220 A | 12/1998 | Elsberry |
| 5,851,508 A | 12/1998 | Greff et al. |
| 5,853,366 A | 12/1998 | Dowlatshahi |
| 5,865,806 A | 2/1999 | Howell |
| 5,869,080 A | 2/1999 | McGregor et al. |
| 5,871,501 A | 2/1999 | Leschinsky et al. |
| 5,876,340 A | 3/1999 | Tu et al. |
| 5,879,357 A | 3/1999 | Heaton et al. |
| 5,891,558 A | 4/1999 | Bell et al. |
| 5,897,507 A | 4/1999 | Kortenbach et al. |
| 5,902,310 A | 5/1999 | Foerster et al. |
| 5,911,705 A | 6/1999 | Howell |
| 5,916,164 A | 6/1999 | Fitzpatrick et al. |
| 5,921,933 A | 7/1999 | Sarkis et al. |
| 5,922,024 A | 7/1999 | Janzen et al. |
| 5,928,626 A | 7/1999 | Klaveness et al. |
| 5,928,773 A | 7/1999 | Andersen |
| 5,941,439 A | 8/1999 | Kammerer et al. |
| 5,941,890 A | 8/1999 | Voegele et al. |
| 5,942,209 A | 8/1999 | Leavitt et al. |
| 5,948,425 A | 9/1999 | Janzen et al. |
| 5,954,670 A | 9/1999 | Baker |
| 5,972,817 A | 10/1999 | Haines et al. |
| 5,980,564 A | 11/1999 | Stinson |
| 5,989,265 A | 11/1999 | Bouquet De La Joliniere et al. |
| 6,015,541 A | 1/2000 | Greff et al. |
| 6,030,333 A | 2/2000 | Sioshansi et al. |
| 6,053,925 A | 4/2000 | Barnhart |
| 6,056,700 A | 5/2000 | Burney et al. |
| 6,066,122 A | 5/2000 | Fisher |
| 6,066,325 A | 5/2000 | Wallace et al. |
| 6,071,301 A | 6/2000 | Cragg et al. |
| 6,071,310 A | 6/2000 | Picha et al. |
| 6,071,496 A | 6/2000 | Stein et al. |
| 6,090,996 A | 7/2000 | Li |
| 6,096,065 A | 8/2000 | Crowley |
| 6,096,070 A | 8/2000 | Ragheb et al. |
| 6,106,473 A | 8/2000 | Violante et al. |
| 6,117,108 A | 9/2000 | Woehr et al. |
| 6,120,536 A | 9/2000 | Ding et al. |
| 6,142,955 A | 11/2000 | Farascioni et al. |
| 6,159,240 A | 12/2000 | Sparer et al. |
| 6,159,445 A | 12/2000 | Klaveness et al. |
| 6,161,034 A | 12/2000 | Burbank et al. |
| 6,162,192 A | 12/2000 | Cragg et al. |
| 6,173,715 B1 | 1/2001 | Sinanan et al. |
| 6,174,330 B1 | 1/2001 | Stinson |
| 6,177,062 B1 | 1/2001 | Stein et al. |
| 6,181,960 B1 | 1/2001 | Jensen et al. |
| 6,183,497 B1 | 2/2001 | Sing et al. |
| 6,190,350 B1 | 2/2001 | Davis et al. |
| 6,190,353 B1 | 2/2001 | Makower et al. |
| 6,200,258 B1 | 3/2001 | Slater et al. |
| 6,203,524 B1 | 3/2001 | Burney et al. |
| 6,203,568 B1 | 3/2001 | Lombardi et al. |
| 6,213,957 B1 | 4/2001 | Milliman et al. |
| 6,214,045 B1 | 4/2001 | Corbitt, Jr. et al. |
| 6,214,315 B1 | 4/2001 | Greff et al. |
| 6,220,248 B1 | 4/2001 | Voegele et al. |
| 6,224,630 B1 | 5/2001 | Bao et al. |
| 6,228,049 B1 | 5/2001 | Schroeder et al. |
| 6,228,055 B1 | 5/2001 | Foerster et al. |
| 6,231,615 B1 | 5/2001 | Preissman |
| 6,234,177 B1 | 5/2001 | Barsch |
| 6,241,687 B1 | 6/2001 | Voegele et al. |
| 6,241,734 B1 | 6/2001 | Scribner et al. |
| 6,251,418 B1 | 6/2001 | Ahern et al. |
| 6,261,243 B1 | 7/2001 | Burney et al. |
| 6,261,302 B1 | 7/2001 | Voegele et al. |
| 6,264,917 B1 | 7/2001 | Klaveness et al. |
| 6,270,464 B1 | 8/2001 | Fulton, III et al. |
| 6,270,472 B1 | 8/2001 | Antaki et al. |
| 6,287,278 B1 | 9/2001 | Woehr et al. |
| 6,287,332 B1 | 9/2001 | Bolz et al. |
| 6,289,229 B1 | 9/2001 | Crowley |
| 6,306,154 B1 | 10/2001 | Hudson et al. |
| 6,312,429 B1 | 11/2001 | Burbank et al. |
| 6,316,522 B1 | 11/2001 | Loomis et al. |
| 6,335,029 B1 | 1/2002 | Kamath et al. |
| 6,336,904 B1 | 1/2002 | Nikolchev |
| 6,340,367 B1 | 1/2002 | Stinson et al. |
| 6,343,227 B1 | 1/2002 | Crowley |
| 6,347,240 B1 | 2/2002 | Foley et al. |
| 6,347,241 B2 | 2/2002 | Burbank et al. |
| 6,350,244 B1 | 2/2002 | Fisher |
| 6,350,274 B1 | 2/2002 | Li |
| 6,354,989 B1 | 3/2002 | Nudeshima |
| 6,356,112 B1 | 3/2002 | Tran et al. |
| 6,356,782 B1 | 3/2002 | Sirimanne et al. |
| 6,358,217 B1 | 3/2002 | Bourassa |
| 6,363,940 B1 | 4/2002 | Krag |
| 6,371,904 B1 | 4/2002 | Sirimanne et al. |
| 6,394,965 B1 | 5/2002 | Klein |
| 6,403,758 B1 | 6/2002 | Loomis |
| 6,405,733 B1 | 6/2002 | Fogarty et al. |
| 6,409,742 B1 | 6/2002 | Fulton, III et al. |
| 6,424,857 B1 | 7/2002 | Henrichs et al. |
| 6,425,903 B1 | 7/2002 | Voegele |
| 6,427,081 B1 | 7/2002 | Burbank et al. |
| 6,436,030 B2 | 8/2002 | Rehil |
| 6,450,937 B1 | 9/2002 | Mercereau et al. |
| 6,450,938 B1 | 9/2002 | Miller |
| 6,471,700 B1 | 10/2002 | Burbank et al. |
| 6,478,790 B2 | 11/2002 | Bardani |
| 6,506,156 B1 | 1/2003 | Jones et al. |
| 6,511,468 B1 | 1/2003 | Cragg et al. |
| 6,537,193 B1 | 3/2003 | Lennox |
| 6,540,981 B2 | 4/2003 | Klaveness et al. |
| 6,544,185 B2 | 4/2003 | Montegrande |
| 6,551,253 B2 | 4/2003 | Worm et al. |
| 6,554,760 B2 | 4/2003 | Lamoureux et al. |
| 6,562,317 B2 | 5/2003 | Greff et al. |
| 6,564,806 B1 | 5/2003 | Fogarty et al. |
| 6,565,551 B1 | 5/2003 | Jones et al. |
| 6,567,689 B2 | 5/2003 | Burbank et al. |
| 6,575,888 B2 | 6/2003 | Zamora et al. |
| 6,575,991 B1 | 6/2003 | Chesbrough et al. |
| 6,585,773 B1 | 7/2003 | Xie |
| 6,605,047 B2 | 8/2003 | Zarins et al. |
| 6,610,026 B2 | 8/2003 | Cragg et al. |
| 6,613,002 B1 | 9/2003 | Clark et al. |
| 6,616,630 B1 | 9/2003 | Woehr et al. |
| 6,626,850 B1 | 9/2003 | Chau et al. |
| 6,628,982 B1 | 9/2003 | Thomas et al. |
| 6,636,758 B2 | 10/2003 | Sanchez et al. |
| 6,638,234 B2 | 10/2003 | Burbank et al. |
| 6,638,308 B2 | 10/2003 | Corbitt, Jr. et al. |
| 6,652,442 B2 | 11/2003 | Gatto |
| 6,656,192 B2 | 12/2003 | Espositio et al. |
| 6,662,041 B2 | 12/2003 | Burbank et al. |
| 6,699,205 B2 | 3/2004 | Fulton, III et al. |
| 6,712,774 B2 | 3/2004 | Voegele et al. |
| 6,712,836 B1 | 3/2004 | Berg et al. |
| 6,716,444 B1 | 4/2004 | Castro et al. |
| 6,725,083 B1 | 4/2004 | Burbank et al. |
| 6,730,042 B2 | 5/2004 | Fulton et al. |
| 6,730,044 B2 | 5/2004 | Stephens et al. |
| 6,746,661 B2 | 6/2004 | Kaplan |

(56) References Cited

U.S. PATENT DOCUMENTS

| | | |
|---|---|---|
| 6,746,773 B2 | 6/2004 | Llanos et al. |
| 6,752,154 B2 | 6/2004 | Fogarty et al. |
| 6,766,186 B1 | 7/2004 | Hoyns et al. |
| 6,774,278 B1 | 8/2004 | Ragheb et al. |
| 6,780,179 B2 | 8/2004 | Lee et al. |
| 6,824,507 B2 | 11/2004 | Miller |
| 6,824,527 B2 | 11/2004 | Gollobin |
| 6,846,320 B2 | 1/2005 | Ashby et al. |
| 6,862,470 B2 | 3/2005 | Burbank et al. |
| 6,863,685 B2 | 3/2005 | Davila et al. |
| 6,881,226 B2 | 4/2005 | Corbitt, Jr. et al. |
| 6,899,731 B2 | 5/2005 | Li et al. |
| 6,918,927 B2 | 7/2005 | Bates et al. |
| 6,936,014 B2 | 8/2005 | Vetter et al. |
| 6,939,318 B2 | 9/2005 | Stenzel |
| 6,945,973 B2 | 9/2005 | Bray |
| 6,951,564 B2 | 10/2005 | Espositio et al. |
| 6,992,233 B2 | 1/2006 | Drake et al. |
| 6,993,375 B2 | 1/2006 | Burbank et al. |
| 6,994,712 B1 | 2/2006 | Fisher et al. |
| 6,996,433 B2 | 2/2006 | Burbank et al. |
| 7,001,341 B2 | 2/2006 | Gellman et al. |
| 7,008,382 B2 | 3/2006 | Adams et al. |
| 7,014,610 B2 | 3/2006 | Koulik |
| 7,025,765 B2 | 4/2006 | Balbierz et al. |
| 7,044,957 B2 | 5/2006 | Foerster et al. |
| 7,047,063 B2 | 5/2006 | Burbank et al. |
| 7,083,576 B2 | 8/2006 | Zarins et al. |
| 7,125,397 B2 | 10/2006 | Woehr et al. |
| 7,160,258 B2 | 1/2007 | Imran et al. |
| 7,172,549 B2 | 2/2007 | Slater et al. |
| 7,214,211 B2 | 5/2007 | Woehr et al. |
| 7,229,417 B2 | 6/2007 | Foerster et al. |
| 7,236,816 B2 | 6/2007 | Kumar et al. |
| 7,264,613 B2 | 9/2007 | Woehr et al. |
| 7,294,118 B2 | 11/2007 | Saulenas et al. |
| 7,297,725 B2 | 11/2007 | Winterton et al. |
| 7,329,402 B2 | 2/2008 | Unger et al. |
| 7,329,414 B2 | 2/2008 | Fisher et al. |
| 7,416,533 B2 | 8/2008 | Gellman et al. |
| 7,424,320 B2 | 9/2008 | Chesbrough et al. |
| 7,449,000 B2 | 11/2008 | Adams et al. |
| 7,527,610 B2 | 5/2009 | Erickson |
| 7,534,452 B2 | 5/2009 | Chernomorsky et al. |
| 7,569,065 B2 | 8/2009 | Chesbrough et al. |
| 7,577,473 B2 | 8/2009 | Davis et al. |
| 7,637,948 B2 | 12/2009 | Corbitt, Jr. |
| 7,651,505 B2 | 1/2010 | Lubock et al. |
| 7,877,133 B2 | 1/2011 | Burbank et al. |
| 2001/0006616 A1 | 7/2001 | Leavitt et al. |
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton, III et al. |
| 2002/0077687 A1 | 6/2002 | Ahn |
| 2002/0082517 A1 | 6/2002 | Klein |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |
| 2002/0188196 A1* | 12/2002 | Burbank et al. ............ 600/431 |
| 2002/0193815 A1 | 12/2002 | Foerster et al. |
| 2002/0193867 A1 | 12/2002 | Gladdish, Jr. et al. |
| 2003/0032969 A1 | 2/2003 | Gannoe et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1 | 10/2003 | Ferrera et al. |
| 2003/0225420 A1 | 12/2003 | Wardle |
| 2003/0233101 A1 | 12/2003 | Lubock et al. |
| 2003/0236573 A1 | 12/2003 | Evans et al. |
| 2004/0001841 A1 | 1/2004 | Nagavarapu et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0101548 A1 | 5/2004 | Pendharkar |
| 2004/0106891 A1 | 6/2004 | Langan et al. |
| 2004/0116802 A1 | 6/2004 | Jessop et al. |
| 2004/0124105 A1 | 7/2004 | Seiler et al. |
| 2004/0127765 A1 | 7/2004 | Seiler et al. |
| 2004/0133124 A1 | 7/2004 | Bates et al. |
| 2004/0162574 A1 | 8/2004 | Viola |
| 2004/0167619 A1 | 8/2004 | Case et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236212 A1 | 11/2004 | Jones et al. |
| 2004/0236213 A1 | 11/2004 | Jones et al. |
| 2005/0020916 A1 | 1/2005 | MacFarlane et al. |
| 2005/0033157 A1 | 2/2005 | Klein et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0113659 A1 | 5/2005 | Pothier et al. |
| 2005/0119562 A1 | 6/2005 | Jones et al. |
| 2005/0143650 A1 | 6/2005 | Winkel |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0208122 A1 | 9/2005 | Allen et al. |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0025677 A1 | 2/2006 | Verard et al. |
| 2006/0025795 A1 | 2/2006 | Chesbrough et al. |
| 2006/0036158 A1 | 2/2006 | Field et al. |
| 2006/0036159 A1 | 2/2006 | Sirimanne et al. |
| 2006/0036165 A1 | 2/2006 | Burbank et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0116573 A1 | 6/2006 | Field et al. |
| 2006/0122503 A1 | 6/2006 | Burbank et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0241411 A1 | 10/2006 | Field et al. |
| 2006/0292690 A1 | 12/2006 | Liu et al. |
| 2007/0021642 A1 | 1/2007 | Lamoureux et al. |

(56) References Cited

U.S. PATENT DOCUMENTS

| | | |
|---|---|---|
| 2007/0038145 A1 | 2/2007 | Field |
| 2007/0057794 A1 | 3/2007 | Gisselberg et al. |
| 2007/0083132 A1 | 4/2007 | Sharrow |
| 2007/0087026 A1 | 4/2007 | Field |
| 2007/0106152 A1 | 5/2007 | Kantrowitz et al. |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0287933 A1 | 12/2007 | Phan et al. |
| 2008/0033280 A1 | 2/2008 | Lubock et al. |
| 2008/0039819 A1 | 2/2008 | Jones et al. |
| 2008/0091120 A1 | 4/2008 | Fisher |
| 2008/0097199 A1 | 4/2008 | Mullen |
| 2008/0188768 A1 | 8/2008 | Zarins et al. |
| 2008/0249436 A1 | 10/2008 | Darr |
| 2008/0269638 A1 | 10/2008 | Cooke et al. |
| 2008/0294039 A1 | 11/2008 | Jones et al. |
| 2009/0000629 A1 | 1/2009 | Hornscheidt et al. |
| 2009/0024225 A1 | 1/2009 | Stubbs |
| 2009/0030309 A1 | 1/2009 | Jones et al. |
| 2009/0069713 A1 | 3/2009 | Adams et al. |
| 2009/0076484 A1 | 3/2009 | Fukaya |
| 2009/0093714 A1 | 4/2009 | Chesbrough et al. |
| 2009/0131825 A1 | 5/2009 | Burbank et al. |
| 2009/0171198 A1 | 7/2009 | Jones et al. |
| 2009/0216118 A1 | 8/2009 | Jones et al. |
| 2010/0010341 A1 | 1/2010 | Talpade et al. |
| 2010/0030149 A1 | 2/2010 | Carr, Jr. |
| 2011/0184280 A1 | 7/2011 | Jones et al. |
| 2012/0078092 A1 | 3/2012 | Jones et al. |
| 2012/0116215 A1 | 5/2012 | Jones et al. |

FOREIGN PATENT DOCUMENTS

| | | |
|---|---|---|
| EP | 0255123 A2 | 2/1988 |
| EP | 0292936 A2 | 11/1988 |
| EP | 0458745 A1 | 11/1991 |
| EP | 0475077 A2 | 3/1992 |
| EP | 0552924 A1 | 7/1993 |
| EP | 0769281 A2 | 4/1997 |
| EP | 1114618 A2 | 7/2001 |
| EP | 1163888 A1 | 12/2001 |
| EP | 1281416 A2 | 6/2002 |
| EP | 1364628 A1 | 11/2003 |
| EP | 1493451 A1 | 1/2005 |
| EP | 1767167 A2 | 3/2007 |
| FR | 2646674 A3 | 11/1990 |
| GB | 708148 | 4/1954 |
| JP | 2131757 A | 5/1990 |
| WO | 8906978 A1 | 8/1989 |
| WO | 9112823 A1 | 9/1991 |
| WO | 9314712 A1 | 8/1993 |
| WO | 9317671 A1 | 9/1993 |
| WO | 9317718 A1 | 9/1993 |
| WO | 9416647 A1 | 8/1994 |
| WO | 9507057 A1 | 3/1995 |
| WO | 9806346 A1 | 2/1998 |
| WO | 9908607 A1 | 2/1999 |
| WO | 9935966 A1 | 7/1999 |
| WO | 9951143 A1 | 10/1999 |
| WO | 0023124 A1 | 4/2000 |
| WO | 0024332 A1 | 5/2000 |
| WO | 0028554 A1 | 5/2000 |
| WO | 0054689 A1 | 9/2000 |
| WO | 0108578 A1 | 2/2001 |
| WO | 0170114 A1 | 9/2001 |
| WO | 0207786 A2 | 1/2002 |
| WO | 03000308 A1 | 1/2003 |
| WO | 2004045444 A2 | 6/2004 |
| WO | 2005013832 A1 | 2/2005 |
| WO | 2005089664 A1 | 9/2005 |
| WO | 2006012630 A2 | 2/2006 |
| WO | 2006056739 A2 | 6/2006 |
| WO | 2006097331 A2 | 9/2006 |
| WO | 2006105353 A2 | 10/2006 |
| WO | 2007069105 A2 | 6/2007 |
| WO | 2008077081 A2 | 6/2008 |

OTHER PUBLICATIONS

Johnson & Johnson: Breast Biopsy (minimally invasive): Surgical Technique: Steps in the MAMOTOME Surgical Procedure. From http://www.jnjgateway.com. 3 pages.

Johnson & Johnson: New Minimally Invasive Breast Biopsy Device Receives Marketing Clearance in Canada; Aug. 6, 1999. From http://www.jnjgateway.com. 4 pages.

Johnson & Johnson: MAMMOTOME HAND HELD Receives FDA Marketing Clearance for Minimally Invasive Breast Biopises; Sep. 1, 1999. From From http://www.jnjgateway.com. 5 pages.

Johnson & Johnson: The Mammotome Breast Biopsy System. From: http://www.breastcareinfo.com/aboutm.htm. 6 pages.

Cook Incorporated: Emoblization and Occlusion. From: www.cookgroup.com 6 pages.

Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.

Armstong, J.S., et al., "Differential marking of Excision Planes in Screened Breast lesions By Organically Coloured Gelatins", Journal of Clinical Pathology, Jul. 1990, No. 43 (7) pp. 604-607, XP000971447 abstract; tables 1,2.

Fucci, V., et al., "Large Bowel Transit Times Using Radioopaque Markers in Normal Cats", J. of Am. Animal Hospital Assn., Nov.-Dec. 1995 31 (6) 473-477.

Schindlbeck, N.E., et al., "Measurement of Colon Transit Time", J. of Gastroenterology, No. 28, pp. 399-404, 1990.

Shiga, et al., Preparation of Poly(D, L-lactide) and Copoly(lactide-glycolide) Microspheres of Uniform Size, J. Pharm. Pharmacol. 1996 48:891-895.

Eiselt, P. et al, "Development of Technologies Aiding Large-Tissue Engineering", Biotechnol. Prog., vol. 14, No. 1, pp. 134-140, 1998.

Fajardo, Laurie, et al., "Placement of Endovascular Embolization Microcoils to Localize the Site of Breast Lesions Removed at Stereotactic Core Biopsy", Radiology, Jan. 1998, pp. 275-278, vol. 206—No. 1.

H. J. Gent, M.D., et al., Stereotaxic Needle Localization and Cytological Diagnosis of Occult Breast Lesions, Annals of Surgery, Nov. 1986, pp. 580-584, vol. 204—No. 5.

Meuris, Bart, "Calcification of Aortic Wall Tissue in Prosthetic Heart Valves: Initiation, Influencing Factors and Strategies Towards Prevention", Thesis, 2007, pp. 21-36, Leuven University Press; Leuven, Belgium.

* cited by examiner

MULTIPLE IMAGING MODE TISSUE MARKER

PRIORITY DATA AND INCORPORATION BY REFERENCE

This application is a U.S. nation phase of International Application No. PCT/US2007/087211, filed Dec. 12, 2007, which claims priority to U.S. Provisional Patent Application No. 60/869,636, filed Dec. 12, 2006, which are incorporated herein by reference in their entirety.

TECHNICAL FIELD

The invention relates generally to a biopsy tissue markers. More specifically, the invention further relates to a biocompatible tissue site marker that is visible under various modes of imaging.

BACKGROUND ART

Advances in modern medical imaging technologies such as X-ray, ultrasound, or magnetic resonance imaging make it possible to identify and to biopsy tumors while they are still small. When dealing with a small tumor, especially after a portion of the tumor has been removed for biopsy, it is sometimes difficult to locate the tumor at a later time for treatment. This is particularly true in the case of tumors in the breast, where the ability to visualize a small growth may depend upon the manner in which the breast is positioned or compressed during the procedure. In addition, prior to surgically removing a tumor, it is often advantageous to try to shrink the tumor by chemotherapy or irradiation. This is especially true in the case of breast cancer, where conservation of breast tissue is a concern. Shrinkage of the tumor can sometimes make it difficult for the surgeon to locate the tumor.

A solution to this problem is to place a marker within the target tissues at the time of biopsy which can be visualized under a variety of imaging modalities to facilitate finding the tumor at a later time. When a suspicious mass is detected, a sample is taken by biopsy, often, but not necessarily, using a specialized instrument such as a biopsy needle. The needle is inserted in the breast while the position of the needle is monitored using fluoroscopy, ultrasonic imaging, X-rays, MRI or other suitable imaging modalities.

In a new procedure, called stereotactic needle biopsy, the breast is compressed between the plates of a mammography apparatus and two separate X-rays are taken from different points of reference. The exact position of the mass or lesion is calculated within the breast. The coordinates of the lesion are then programmed into a mechanical stereotactic apparatus which guides the biopsy needle to the lesion.

Irrespective of the biopsy technique, the surgical site may need to be examined or accessed for surgical treatment of a cancerous lesion. Treatment requires the surgeon or radiologist locate the lesion precisely and this may need to be done repeatedly over a period of time. Since treatment may alter the host tissue, the function of a marker even more important.

U.S. Pat. No. 6,725,083 for "Tissue site markers for in vivo imaging" describes biopsy site markers and methods that permit conventional imaging techniques to be used, such as ultrasonic imaging. The biopsy site markers have high ultrasound reflectivity due to high contrast of acoustic impedance resulting from gas-filled internal pores. The markers may have a non-uniform surface. The patent discloses the use of materials such as metal, ceramic materials, metal oxides, polymer, and composites and mixtures thereof.

U.S. Pat. No. 6,350,244 for "Bioabsorable markers for use in biopsy procedure" discloses a breast tissue marker that allows the marker to be left in place avoiding the need for surgical removal. One type of marker takes the form of hollow spheres made of polylactite acid filled with iodine or other radiopaque material to make them visible under X-rays and/or ultrasound. The radiopaque materials are also bioabsorbable. Another type of marker disclosed is a solid marker of pre-mixed radiopaque material and a bioabsorbable material. The solid markers may also include dyes and radioactive materials.

U.S. Pat. No. 6,347,241 for "Ultrasonic and x-ray detectable biopsy site marker and apparatus for applying it" shows a biopsy site marker of small bodies or pellets of gelatin which enclose substantially a radioopaque object. The pellets are deposited at the biopsy site by an applicator device inserted in the biopsy site. Several gelatin pellets are deposited through the tube. The radio opaque core in the gelatin bodies are of a non-biological material and structure which are readily identified during X-ray observations.

U.S. Pat. No. 6,161,034 for "Methods and chemical preparations for time-limited marking of biopsy sites" describes markers that remain present to permit detection and location of the biopsy site. The markers are later absorbed by the host. The patent discloses gelatin, collagen, balloons and detectability provided by AgCl; AgI; $BaCO_3$; $BaSO_4$; K; $CaCO_3$; ZnO; $Al_2O_3$; and combinations of these.

US Patent Publication No. 2006/0079805 for "Site marker visible under multiple modalities" describes site markers that include balls or particles which are bonded together to form a marker body. The balls or particles are made from biocompatible materials such as titanium, stainless steel or platinum. The balls or particles are described as being bonded together by sintering or by adhesive such as epoxy. An alternative embodiment has at least one continuous strand of wire of biocompatible material such as titanium, stainless steel, platinum, or other suitable material, compressed to form a mass that resembles a ball of yarn. Another alternative is a resonating capsule, or a rod with drilled holes.

US Patent Publication No. 2006/0036165 for "Tissue site markers for in vivo imaging" shows ultrasound-detectable markers whose shapes are distinct in an image from biological shapes. Various shapes are disclosed including cylinders, coils, and other more complex shapes.

It is believed that most known tissue markers have a disadvantage in that they are not visible under all available imaging modalities. The features of a marker that make it stand out under X-rays do not necessarily make them stand out under MRI or ultrasound imaging. One prior art mechanism for addressing the need for multiple-imaging-mode markers is to employ a combination of metal structure and biodegradable foam to provide ultrasonic imaging visibility, MRI visibility and x-ray visibility. In this case, the metal structure provides x-ray visibility and biodegradable foam provides visibility in ultrasonic imaging.

There is a need for site markers made from biocompatible materials that are visible under various modes of imaging to reduce the number of procedures that patients must undergo in detection and treatment of cancer or any disease requiring the user of tissue markers. It will be a valuable contribution to the art for a marker with a simple design and superior biocompatibility can be provided. Also, selectable bioabsorability by the host may be an advantage as well.

SUMMARY OF THE INVENTION

A hydroxyapatite or porous metal or non-metal-based biopsy marker is visible in multiple imaging modalities. In a preferred embodiment, hydroxyapatite, a component of natural bone, is used. This material is highly visible when viewed using X-ray imaging. The ultrasonic visibility may be provided by creating one or more voids within the hydroxyapatite marker and entrapping a biocompatible gas within the void or voids. The biocompatible gas provides a low density structure within the marker body which provides high contrast when viewed using ultrasonic imaging equipment. Also, hydroxyapatite has the advantage of being very biocompatible. In addition, if biodegradability is desired, hydroxyl apatite is capable of being rendered in a form that makes it long-lasting, but ultimately biodegradable as well.

The manufacture of porous hydroxyapatite performs or molded forms is well known. The hydroxyapatite can be made porous by many methods known in ceramic manufacturing art. These methods include but not limited to: molding the hydroxyapatite particles to a desired geometry and then sintering the green mass. The preferred porosity levels in porous Hydroxyapatite could range from 30% to 80%, and more preferably, from 60 to 80%. One exemplary method is to mix powdered hydroxyapatite with a removable material to form a slurry which when hardened can be removed and then to sinter the hydroxyapatite to form a porous structure. Examples of removable material include various soluble polymers, naphthalene, and others. Purified hydroxyapatite powder can be made from known processes or obtained from natural sources such as coral.

In an embodiment, a porous hydroxyapatite article may be obtained, for example from commercial sources such as Berkeley Advanced Biomaterials, Inc and incubated in carbon dioxide atmosphere to fill the pores. The disk is visible under X-ray and ultrasonic imaging.

Material other than hydroxyapatite can be used to make a marker visible under multiple imaging modalities. For example, a biocompatible porous ceramic may be used alone or in combination with a biocompatible impermeable jacket, such as a coating of PTFE. The porous ceramic material can be produced by sintering particles with a sufficient void fraction to make the resulting article distinct under ultrasound. Ceramics containing mixtures of materials may be employed to enhance radio-opacity. For example, ceramics can contain metallic inclusions. Ceramic particles (or metal-ceramic particle mixtures) having a packing density of a desired fraction, for example 70%, may be sintered to create a mass. The result may have no, or limited, connections between the void spaces so that the result needs no impermeable jacket to avoid the voids filling with fluids. Alternatively, a coating may be provided to prevent ingress of fluids. The coating need not be mechanically continuous over the article if it is sufficient to retard ingress of moisture. For example, the coating material may be hydrophobic. In a variation, techniques used for making refractory foams may be employed to create a marker.

In another embodiment, a biocompatible porous metal is used in place of hydroxyapatite. The porous metal can be produced by mechanical methods known in the art such as sand blasting. Other methods such as laser etching, chemical etching or powder metallurgical methods including sintering could also be used. In one preferred approach, porous metals are obtained by compacting a metal powder to a desired shape in presence of a polymeric and non-polymeric binder and then sintering the metal powder particles to form a homogenous metal mass with predetermined porosity/density. Many metals and alloys suitable for long term implant could be used and these include but not limited to: Nitinol, gold, silver, stainless steel, cobalt-chromium alloy, titanium, tantalum, and tungsten or combination thereof.

The shape and geometry of the porous biopsy marker can depend on the clinical application. In general cylindrical, spherical, disk like shapes are preferred. Irregular shapes may also be used.

According to an embodiment, an intracorporeal marker marks a site within living tissue of a host. The marker has a body of porous hydroxyapatite whose size and shape permit visualization under ultrasonic and radiation imaging modalities. Preferably, the shape is generally cylindrical. In one embodiment, the marker has a lower density core region and a higher density surface region.

According to an embodiment, an intracorporeal marker marks a site within living tissue of a host. The marker has an ultrasound-detectable portion defined by boundaries that are distinctly different from normal tissue features. The ultrasound-detectable portion is of a material that exhibits high contrast in acoustical impedance compared to the host tissue. The same portion, or a different portion, of a material exhibits high contrast in at least one type of radiation imaging. The portion or the same or different portion includes at least one of porous ceramic, a porous metal, and a porous hydroxyapatite.

In a variation, the shape is generally cylindrical. In another variation, the marker has a lower density core region and a higher density surface region. A water-impermeable coating layer may be provided to seal the marker against penetration by fluid, particularly where the voids within are channeling voids. In a particular embodiment the marker is of hydroxyapatite and in a further, more specific variation, the surface region of the marker has a higher density.

According to an embodiment, an intracorporeal marker for marking a site within living tissue of a host has a porous body of hydroxyapatite. The pores of the porous body are of such a size as to maximize the visibility of the body under ultrasonic imaging. In a variant, the body has a surface of higher density than a major fraction beneath the surface.

According to an embodiment, an intracorporeal marker marks a site within living tissue of a host. The marker includes a body of porous hydroxyapatite whose physical properties permit the body to be distinguished from human soft tissue under visualization using ultrasonic and radiation imaging modalities. The body can have various shapes, a preferred shape is a cylindrical shape. In a preferred embodiment, the body has gas-filled pores. In another preferred embodiment, the body has a core and a surface region, the core region having a lower density than the surface region.

Note that, as used in this specification, the term soft tissue is intended to characterize non-skeletal tissue which relatively transparent to X-rays such that tissue such as bone and some ligaments, cartilage, and fibrous tissue can be distinguished from it. Thus, a hydroxyapatite marker may be substantially visible under X-rays when placed in soft-tissue but might be hard to distinguish from non-soft-tissue.

According to another embodiment, an intracorporeal marker marks a site within living tissue of a host. The body includes at least one material that exhibits detectable difference in acoustical impedance relative to human soft tissue. The at least one material also exhibits detectable difference in radiation impedance relative to human soft tissue. The at least one material includes at least one of porous ceramic and a porous metal. Preferably, the body has a shape that is generally cylindrical. In a variation of the embodiment, the body has a core and a surface region, the core region having a lower density than the surface region. In another variation of the embodiment, the body has a surface and the surface has a water-impermeable coating layer. The at least one material preferably includes hydroxyapatite and preferably the material is solely hydroxyapatite.

According to another embodiment, an intracorporeal marker marks a site within living tissue of a host. The marker has a porous body of hydroxyapatite, the body having pores filled with gas. The sizes of the pores and the gas are such that the body can be visualized under ultrasound. In a variation, the body has a core and a surface region, the core region having a lower density than the surface region.

According to another embodiment, a method of in vivo identification of a position in soft tissue includes inserting a marker containing hydroxyapatite at a position in soft tissue of a living host; passing ultrasonic energy through the soft tissue to form an ultrasound image of the marker; and passing radiant energy through the soft tissue to form an X-ray image of the marker. Preferably, the hydroxyapatite defines a porous structure and more preferably, the body consists substantially of hydroxyapatite.

According to another method of in vivo identification of a position in soft tissue, a marker containing hydroxyapatite is inserted at a position in soft tissue of a living host. Ultrasonic energy is then passed through the living host to form an ultrasound image of the marker. The image is then used to locate a site for a medical treatment. Preferably, the hydroxyapatite is porous. The marker may consist substantially of hydroxyapatite.

According to another embodiment, a method of in vivo identification of a position in soft tissue, includes: inserting a marker containing hydroxyapatite at a position in soft tissue of a living host; passing radiant energy through the living host to form an X-ray image of the marker using the image to locate a site for a medical treatment. Preferably, the hydroxyapatite is porous. The marker may consist substantially of hydroxyapatite.

According to another embodiment, a method of in vivo identification of a position in soft tissue, includes: inserting a marker containing a porous ceramic at a position in soft tissue of a living host; passing ultrasonic energy through the living host to form an ultrasound image of the marker; passing radiant energy through the living host to form an X-ray image of the marker; using the image to locate a site for a medical treatment. Preferably, the porous ceramic includes hydroxyapatite and more preferably, the porous ceramic is substantially made of hydroxyapatite.

According to another embodiment, a method of in vivo identification of a position in soft tissue, includes: inserting a marker containing a porous ceramic at a position in soft tissue of a living host; passing ultrasonic energy through the living host to form an ultrasound image of the marker; passing energy through the living host to form an image of the marker based on a non-ultrasound imaging modality; using the image to locate a site for a medical treatment. Preferably, the porous ceramic includes hydroxyapatite and more preferably, the porous ceramic is substantially made of hydroxyapatite.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DISCLOSURE OF THE INVENTION

Ceramics with voids in them, such as ceramic foams, are often used as filtering materials. Some are used for filtering molten metal, for example. Such materials may be manufactured in a variety of different ways. Ceramic foam filters are generally made by impregnating a polymeric foam with an aqueous slurry of ceramic material containing a binder. The impregnated foam is dried to remove water, and the dried impregnated foam is fired to eliminate the polymer material. This leaves the ceramic foam. This process is often used to create a channelized product but recipe variations, such as a lower quantity of foaming agent, can produce non-channelized product.

Foamed glass methods of manufacture and articles of manufacture are disclosed in U.S. Pat. No. 5,972,817, "Foamed Glass Article for Preparing Surfaces, Use Therefor, and Method of Making Same" to Haines et al.; U.S. Pat. No. 5,821,184, "Foamed Glass Article for Preparing Surfaces, Use Therefore and Method of Making Same" to Haines et al.; U.S. Pat. No. 5,928,773, "Foamed Glass Articles and Methods of Making Same and Methods of Controlling the PH of Same Within Specific Limits" to James C. Andersen; and published US Pat. Appl. No. 20040016195 for "Foamed glass article for use as thermal energy control media;" each of which is hereby incorporated by reference and attached hereto as if fully set forth herein.

Figure 1:
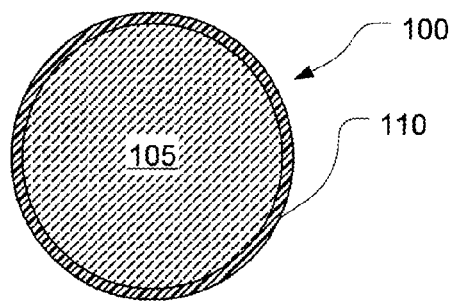
FIG. 1 is a cross-sectional view of a tissue marker with a gas-impermeable (or resistant) casing.
Figure 3:
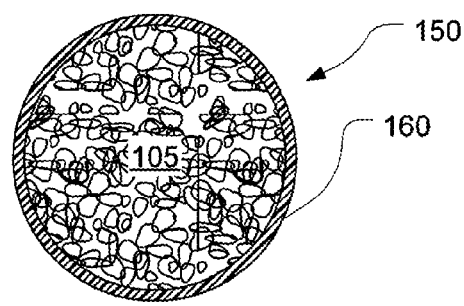
FIG. 3 is a cross-sectional view of a tissue marker with a gas-impermeable or liquid impermeable coating and a porous metal, ceramic, or hydroxyapatite core.
Figure 2:
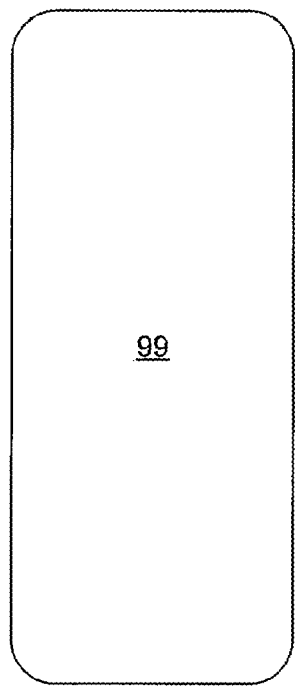
FIG. 2 shows a tissue marker from the side which is cylindrical shape according to exemplary embodiments.

The voids may channel; i.e., they may generally intersect or communicate with each other and the external surface. Alternatively, they may be of a so-called closed cell type where the voids do not communicate with each other or the external surface. In void channeling materials or materials which are naturally rough or porous, it is preferred for the matrix to be hydrophobic or that the surface of the marker be sealed by an impermeable, preferably hydrophobic, coating. This helps to resist filling of the voids or surface pits with aqueous fluid. FIG. 1 illustrates, in section, a marker 100 having a core 105 with a coating 110 overlying its surface. The coating also may promote the biocompatibility of the surface as well as ensure against filling of voids. FIG. 2 illustrates a side view of a marker 99 which is consistent with the embodiment of FIG. 1 as well as with other embodiments disclosed herein. FIG. 3 illustrates a marker with a porous non-ceramic material, such as sintered metal alloy. A coating 160, as described in the embodiment of FIG. 1, may be provided in this particular marker 150.

Figure 4:
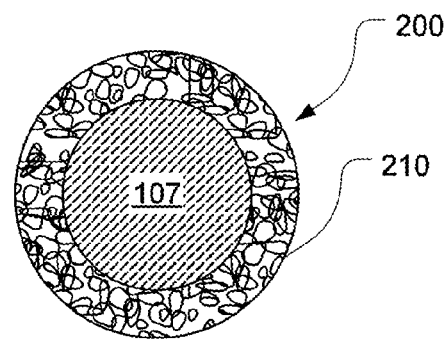
FIG. 4 is a cross-sectional view of a tissue marker with a porous outer layer of metal, ceramic, or hydroxyapatite and a relatively solid metal, ceramic, or hydroxyapatite core.

FIG. 4 illustrates a two-component marker 200 of porous hydroxyapatite 210 on an external layer over a core 107 which may be of a different material, such as one which is predominantly visible under X-ray imaging. The external layer 210 is biocompatible owing to the use of hydroxyapatite. The porosity of the outer layer 210 enhances the marker's visibility under ultrasonic imaging. The outer layer 210 also provides the biocompatibility of hydroxyapatite on the entire outer surface of the marker 200. The core 107 may be metallic, ceramic composite (with metallic material to enhance X-ray absorption), or it may be a non-porous, or a less porous form of the outer layer 210, for example, hydroxyapatite. In an alternative embodiment, the outer layer 210 and core 107 materials discussed with reference to the FIG. 4 embodiment may be reversed. For example, the core 107 may be porous and the outer layer 210 could be solid or relatively more solid than the core.

Figure 5:
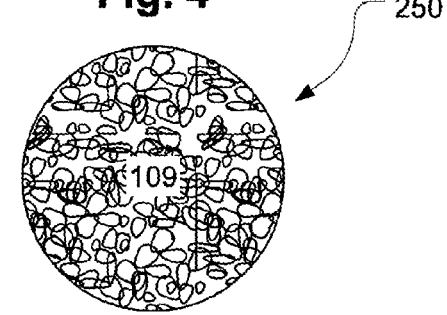
FIG. 5 illustrates a monolithic porous marker, such as of hydroxyapatite.
Figure 6:
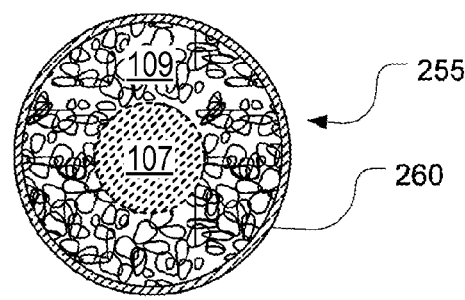
FIG. 6 illustrates the marker of FIG. 5 with a relatively solid outer layer, such as a porous material of the core that has been treated to densify the outer surface region to make it relatively less susceptible to having the gas in the porous gas-filled voids from being displaced by body fluids.
Figure 7:
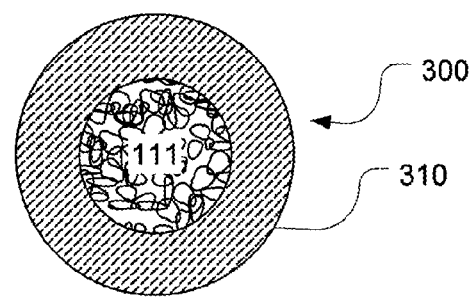
FIG. 7 illustrates a porous core with a relatively solid outer layer which may be of the same or a different material from the core.

FIG. 5 illustrates a preferred embodiment of a single-component porous hydroxyapatite marker 250 which is of porous hydroxyapatite 109 throughout. A marker 255 which is a variation on the embodiment 250 is shown in FIG. 6 in which a core 109 of porous hydroxyapatite is treated on its surface to close any channeling and/or smooth its surface to create a denser outer layer 260 of hydroxyapatite. Another variation of a hydroxyapatite marker is shown in FIG. 7 in which the marker 300 has a porous hydroxyapatite core 111 and a more solid, or completely solid, outer layer 310. Variations of these hydroxyapatite embodiments are also considered useful, for example, a porous outer layer 109 with a non-porous or low porosity core 107 (shown in dashed lines) and as a further alternative a dense core 107 with a porous outer layer 109 that has been treated to form a thin dense outer layer 260 as in the embodiment of FIG. 6. In the latter embodiment, the porosity would change from dense at the center, to porous toward the surface and then back to dense at the surface. Table 1 illustrates various embodiments with H referring to hydroxyapatite, M referring to metal, C referring to ceramic, and J referring to an impermeable coating and the subscripts P and S referring to porous and solid (or relatively low porosity). Note that other combinations may be employed, the table providing merely a summary of some preferred options.

voids may be formed by entrapping a biocompatible gas within the void or voids.

The markers may be incubated in carbon dioxide atmosphere to fill the voids with the gas. As discussed above, various methods may be used to create the hydroxyapatite bodies. These methods include but not limited to: molding the hydroxyapatite particles to a desired geometry and then sintering the green mass. The preferred porosity levels in porous Hydroxyapatite could range from 30% to 80%, and more preferably, from 60 to 80%.

Preferably porous portions are have a sufficient void fraction and a size chosen to ensure the marker is distinct under ultrasonic imaging. Porous ceramic material can be produced by sintering particles with a sufficient void fraction to make the resulting article distinct under ultrasound. As indicated above, ceramics containing mixtures of materials may be employed to enhance radio-opacity. For example, ceramics can contain metallic inclusions. Ceramic particles (or metal-ceramic particle mixtures) having a packing density of a desired fraction, for example 70%, may be sintered to create a mass. The result may have no or limited connections between the void spaces so that the result needs no impermeable jacket to avoid the voids filling with fluids. Alternatively, a coating may be provided to prevent ingress of moisture. The coating need not be mechanically continuous over the article if it is sufficient to retard ingress of moisture. For example, the coating material may be hydrophobic. In a variation, techniques used for making refractory foams may be employed to create a marker.

In embodiments where a biocompatible porous metal is used the metal porosity may be obtained by compacting a metal powder to a desired shape in presence of a polymeric and non-polymeric binder and then sintering the metal powder particles to form a homogenous metal mass with predetermined porosity/density. Many metals and alloys suitable for long term implant could be used and these include but not limited to: Nitinol, gold, silver, stainless steel, cobalt-chromium alloy, titanium, tantalum, and tungsten or combination thereof.

The shape of the marker can depend on the clinical application. In general cylindrical, spherical, disk like shapes are preferred. Irregular shapes may also be used.

According to a feature of the above embodiments, a marker of the any of the above described structures and compositions may be used according to the following

TABLE 1

Structural embodiments of biopsy markers

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Core | $H_P$ | $M_P$ | $C_P$ | $H_S$ | $M_S$ | $C_S$ | $H_P$ | $M_P$ | $C_P$ | $H_S$ | $M_S$ | $C_S$ | $M_P$ | $C_P$ | $M_S$ |
| Outer layer | $H_S$ | $M_S$ | $C_S$ | $H_P$ | $M_P$ | $C_P$ | — | — | — | $H_P$ | — | — | $M_S$ | $C_S$ | — |
| Surface layer | — | — | — | $H_S$ | $M_S$ | $C_S$ | — | J | J | — | — | — | J | J | J |

Although referred to as porous, the materials above may include one or more discrete voids formed non-randomly. For example, the voids may be formed by binding filaments of the marker material together, for example ultrasonic welding of thin wires to form voids in a metal marker or component of a marker. Voids may be also be formed by other processes such as machining, chemical etching, laser etching, etc. In general, where the embodiments are described as being porous, such alternative types of voids, including a single void chamber, are also contemplated. The method which may include steps 1 and 2, steps 1 through 3, or steps 1 through 4, according to different embodiments.

Step 1. Insert a marker at a location. The location can be marked at a time and location of biopsy or otherwise positioned in a tissue mass.

Step 2. Identify a location of the marker using a first imaging modality. The modality may be X-ray-based imaging or ultrasound-based imaging. This step may include passing a corresponding form of energy through a soft tissue mass of a living host.

Step 3. Identify a location of the marker using a second imaging modality that is different from the first imaging modality in step 2. The second imaging modality may be X-ray-based imaging or ultrasound-based imaging. This step may also include passing a corresponding form of energy through a soft tissue mass of a living host.

Step 4. Surgically remove the marker.

Note that while the principal embodiments described above had a generally symmetrical configuration, it is also possible to form asymmetrical embodiments. For example, bodies having different materials that can be imaged using different modalities can be located adjacent each other on respective sides of the body. Also, for example, cylindrical embodiments with a low density portion and high density portion, each on a respective side of the axis in a first embodiment, or each on a respective end of (displaced along the axis) could be provided. Thus, the manner in which material is distributed is not necessarily confined to the particular examples shown. Such embodiments could be imaged using multiple imaging modalities.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

The invention claimed is:

1. An intracorporeal marker, for marking a site within living tissue of a host, comprising:
    a body comprised of first and second distinct materials, the body having a core region made of the first material completely surrounded by an outer region made of the second material, the first material being comprised of porous hydroxyapatite having physical properties that permit the body to be distinguished from human soft tissue under visualization using ultrasonic and radiation imaging modalities, the second material being comprised of a second hydroxyapatite, and wherein the porous hydroxyapatite of the core region has a first porosity and the second hydroxyapatite of the outer region has a second porosity, wherein the first porosity of the porous hydroxyapatite of the core region is higher than the second porosity of the second hydroxyapatite of the outer region.

2. The marker of claim 1, wherein the body has a cylindrical shape.

3. The marker of claim 1, wherein the body has gas-filled pores.

4. The marker of claim 1, wherein the outer region has a surface that is water-impermeable.

5. An intracorporeal marker for marking a site within living tissue of a host, comprising:
    a porous body having a central region and a surface that surrounds the central region, the body having pores filled with gas, the sizes of the pores and the gas being such that the body is configured to be visualized under ultrasound, wherein the porous body comprises a first dense hydroxyapatite at the central region, a second dense hydroxyapatite at the surface, and a porous hydroxyapatite between the central region and the surface, and wherein the porous hydroxyapatite has porosity levels in a range of 30 percent to 80 percent.

6. The intracorporeal marker of claim 5, wherein the hydroxyapatite body changes in porosity from the first dense hydroxyapatite at the central region to the porous hydroxyapatite at the intermediate region and changes in porosity from the porous hydroxyapatite at the intermediate region to the second dense hydroxyapatite at the surface.

7. An intracorporeal tissue marker, comprising first and second distinct materials, the first material comprising a core of the marker and having a first density, the second material completely surrounding the first material and having a second density, the first density being lower than the second density, and wherein each of the first material and the second material comprises hydroxyapatite.

8. The intracorporeal marker of claim 7, wherein the first material comprises a porous hydroxyapatite and the second material comprises hydroxyapatite having a density greater than the porous hydroxyapatite.

9. The intracorporeal marker of claim 7, further comprising a third material completely surrounded by the first material, the first density being lower than the third density.

10. The intracorporeal marker of claim 9, wherein each of the first material, the second material, and the third material comprises hydroxyapatite.

11. The intracorporeal marker of claim 9, wherein the first material comprises porous hydroxyapatite having porosity levels in a range of 30 percent to 80 percent, and each of the second material and the third material comprises hydroxyapatite having a porosity lower than the porous hydroxyapatite.

* * * * *